(12) United States Patent
O'Rourke

(10) Patent No.: US 6,659,100 B2
(45) Date of Patent: *Dec. 9, 2003

(54) SEALED BACK PRESSURE BREATHING DEVICE

(76) Inventor: Sam O'Rourke, 325 Brookmeade Dr., Gretna, LA (US) 70056

(*) Notice: Subject to any disclaimer, the term of this patent is extended or adjusted under 35 U.S.C. 154(b) by 0 days.

This patent is subject to a terminal disclaimer.

(21) Appl. No.: 10/302,384

(22) Filed: Nov. 22, 2002

(65) Prior Publication Data

US 2003/0062047 A1 Apr. 3, 2003

Related U.S. Application Data

(63) Continuation of application No. 09/699,226, filed on Oct. 26, 2000, now Pat. No. 6,510,846, which is a continuation-in-part of application No. 09/471,553, filed on Dec. 23, 1999, now Pat. No. 6,412,481.

(51) Int. Cl.[7] .................. A61M 11/00; A61M 16/00; A62B 9/02
(52) U.S. Cl. .................. 128/200.21; 128/204.18; 128/205.24
(58) Field of Search .................. 128/200.21, 200.24, 128/203.12–203.14, 203.16–203.18, 203.26, 203.28, 204.14, 205.24; 600/538–540, 541; 482/13; 137/907, 908, 493.2

(56) References Cited

U.S. PATENT DOCUMENTS

| | | | |
|---|---|---|---|
| 4,182,366 A | * | 1/1980 | Boehringer .................. 137/510 |
| 4,207,884 A | * | 6/1980 | Isaacson .................. 128/200.24 |
| 4,231,973 A | * | 11/1980 | Young et al. .................. 261/78.2 |
| 4,354,520 A | * | 10/1982 | Easley, Jr. .................. 137/543.23 |
| 4,823,828 A | * | 4/1989 | McGinnis .................. 137/102 |
| 4,854,574 A | * | 8/1989 | Larson et al. .................. 482/13 |
| 5,086,765 A | * | 2/1992 | Levine .................. 128/200.21 |
| 5,099,833 A | * | 3/1992 | Michaels .................. 128/200.14 |
| 5,425,358 A | * | 6/1995 | McGrail et al. .................. 128/205.24 |
| 5,479,920 A | * | 1/1996 | Piper et al. .................. 128/204.23 |
| 5,547,440 A | * | 8/1996 | Rubens et al. .................. 482/13 |
| 5,598,835 A | * | 2/1997 | von Schrader .................. 128/200.21 |
| 5,655,520 A | * | 8/1997 | Howe et al. .................. 128/203.12 |
| 5,890,998 A | * | 4/1999 | Hougen .................. 482/13 |
| 6,083,141 A | * | 7/2000 | Hougen .................. 482/13 |
| 6,343,603 B1 | * | 2/2002 | Tuck et al. .................. 128/205.24 |
| 6,412,481 B1 | * | 7/2002 | Bienvenu et al. .................. 128/200.21 |
| 6,510,846 B1 | * | 1/2003 | O'Rourke .................. 128/200.21 |

* cited by examiner

*Primary Examiner*—Weilun Lo
*Assistant Examiner*—Teena Mitchell
(74) *Attorney, Agent, or Firm*—Keaty Professional Law Corporation

(57) ABSTRACT

A hand-held breathing device for use by patients having respiratory problems creates a sealed backpressure in the airways of the patient by creating resistance to exhalation. A peep valve is mounted inside a hollow body, and a pre-set compression spring is mounted between the valve and an adjustable cap or cam lever in the main body of the device. A pair of valve openings extend through the wall of the main body, one opening serving as an intake port for inhaling of air by the patient and the second port—for exhalation of carbon dioxide. An intake valve is mounted inside the body between a normally open end of the device and the exhalation valve. In one of the embodiments, the device is attached to a nebulizer to facilitate buildup of positive pressure and delivery of medication to the patients' lungs.

9 Claims, 2 Drawing Sheets

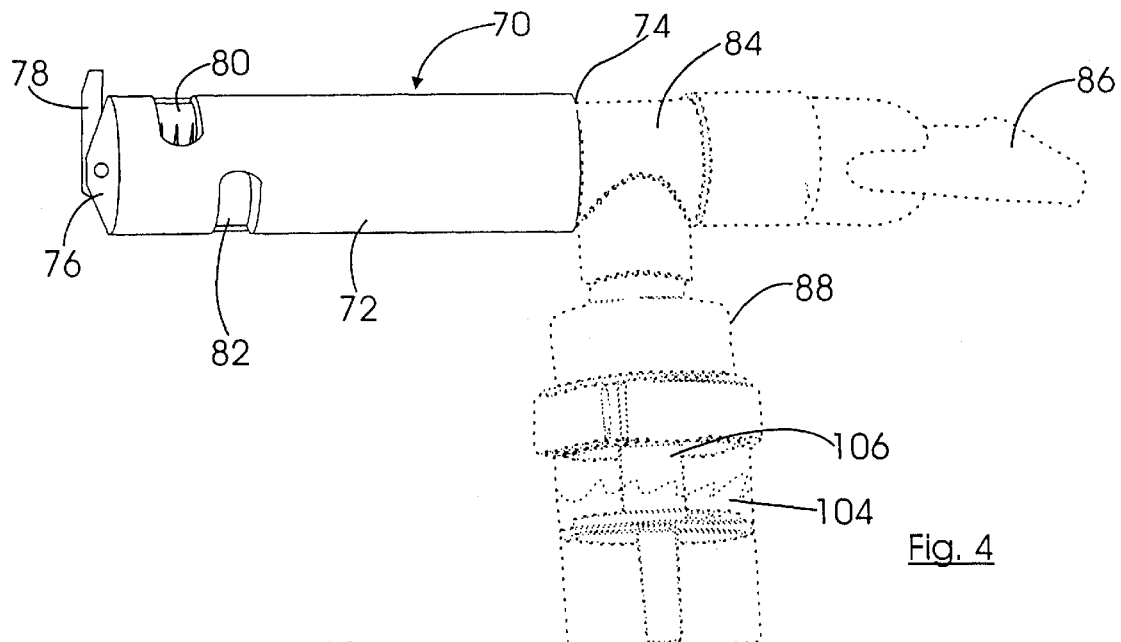
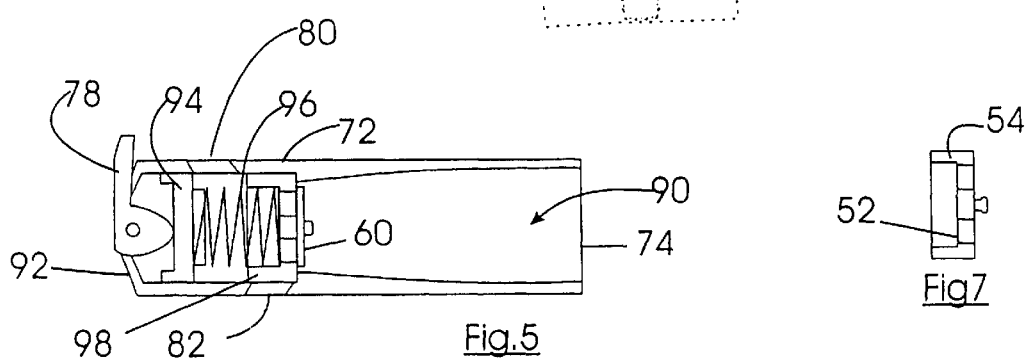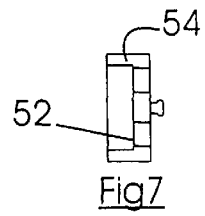
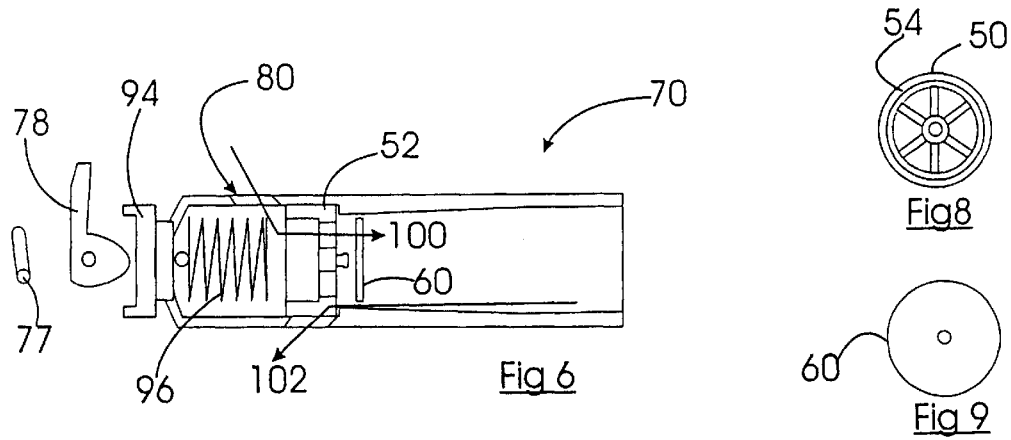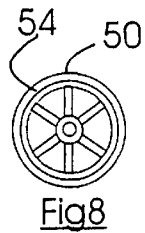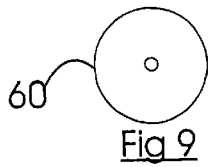

US 6,659,100 B2

SEALED BACK PRESSURE BREATHING DEVICE

CROSS-REFERENCE TO RELATED APPLICATIONS

This application is a continuation of my application Ser. No. 09/699,226 filed on Oct. 26, 2000 for "Sealed Back Pressure Breathing Device," now U.S. Pat. No. 6,510,846 which is a continuation-in-part of my joint application Ser. No. 09/471,553, filed on Dec. 23, 1999, entitled "Sealed Back Pressure Attachment Device for Nebulizer," now U.S. Pat. No. 6,412,481, the full disclosures of which are incorporated by reference herein.

BACKGROUND OF INVENTION

The present invention relates to a device for assisting pulmonary functions of a patient; it can be used alone for exercising muscles involved in breathing or in combination with a nebulizer for delivery of medication to the airways of a patient. More particularly, the present invention relates to a breathing device for generating positive backpressure in the airways of the user so as to keep the airways open and restore normal breathing.

Nebulizers are some of the most widely used devices for assisting patients with breathing problems; they help deliver medication during asthma attacks, emphysema attacks and similar occasions. Nebulizers are conventionally used in emergency rooms, by patients, and medical professionals when conventional method metered dose inhalers (MDIs) fail to reverse a constriction in the airways. The nebulizers break down the liquid medicine into tiny droplets that resemble mist and then deliver the medication into the lungs and airways of the patient.

Conventionally, nebulizers dispense airway dilators. For example, when a patient is brought into an emergency room, he has an unusually high concentration of carbon dioxide in blood. The nebulizer helps deliver the much-needed dilators to the lungs and help expel the gas from the lungs. The dilators contain a chemical that reacts with the receptors in the bronchioles of the patient to open the airways. The medications may include steroids, magnesium sulfate, and bronchodilators.

However, conventional nebulizers are relatively slow, it may require up to eight hours of treatment. When a patient arrives in an acute condition that requires an immediate treatment, an ambu bag with a mask is often used. The mask seals the mouth and nose of the patient; when the bag is squeezed positive pressure forces the medication into the airways. This procedure is not free from complications. Air may be diverted into the patient's stomach and cause gastric distention or vomiting, which in turn increases the risk of aspiration since the vomited medium may be inhaled and forced into the lungs.

Some patients cannot be helped with either nebulizers or ambu bags; they require a ventilator, an artificial breathing machine that works with an endotracheal tube inserted into the trachea of the patient. The positive pressure is much greater than when nebulizer with an ambu bag are used. Often times, excessive air is forced into the patient's lungs. The longer a patient stays on a ventilator, the more difficult it may be to wean the patient from ventilator. Prolonged use of the ventilator tends to cause atrophy of inspiratory muscles, which may become irreversible.

This invention contemplates elimination of drawbacks associated with the prior art and provision of hand-held devices that can be equally used by the patient and by a medical professional for exercising inspiratory muscles and for delivery of medication with the help of a nebulizer.

SUMMARY OF THE INVENTION

It is, therefore, an object of the present invention to provide a sealed calibrated back pressure device that would allow creation of positive pressure on the constricted airways of a patient suffering from asthma, emphysema or other respiratory diseases.

It is another object of the present invention to provide a sealed back pressure breathing attachment device for a nebulizer that can be preset to create the desired amount of pressure and deliver the medication for restoring the patient's breathing.

It is a further object of the present invention to provide a breathing device that would help in exercising inspiratory muscles of a patient.

These and other objects of the present invention are achieved through a provision of a hand-held lightweight device that has a means for adjusting the amount of positive pressure created in the airways of the patient. The device has a hollow body with a peep valve mounted on a bracket inside the hollow body. The hollow body is provided with two through openings: an intake port and an exhalation port. An intake valve, which can be as simple as a rubber gasket, is mounted in the hollow body between the exhalation valve and an open end.

The open end may carry a mouthpiece or be suitably sized and shaped to be connected, via a manifold, to a nebulizer. The opposite closed end of the hollow body carries a means for adjusting the positive pressure. In one of the embodiments, the adjustment means is a cap that threadably engages the hollow body; in the second embodiment—it is an adjustable cam lever. A compression spring is mounted between the exhalation valve and the adjustment means. The calibration may be set to a desired pressure, preferably between 5 cm and 20 cm of water.

BRIEF DESCRIPTION OF THE DRAWINGS

Reference will now be made to the drawings, wherein like parts are designated by like numerals, and wherein

FIG. 4 is a perspective view of the second embodiment of the device in accordance with the present invention mounted on a manifold that connects the device to a nebulizer.

FIG. 5 is a longitudinal sectional view showing the embodiment of FIG. 4 with an adjustable cam lever.

FIG. 6 is a longitudinal sectional view of the second embodiment showing air movement on inspiration and expiration.

FIG. 7 is a detail view showing a support bracket on the expiration valve.

FIG. 8 is a detail front view showing the intake open on the exhalation valve.

FIG. 9 is a detail view showing an intake valve.

DETAILED DESCRIPTION OF THE PREFERRED EMBODIMENT

Figure 1:
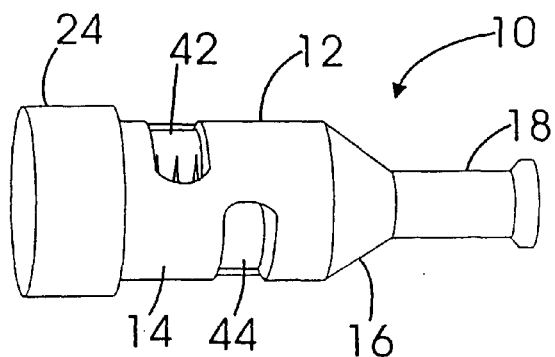
FIG. 1 is a perspective view of the attachment device in accordance with the first embodiment of the present invention.

Turning now to the drawings in more detail, numeral 10 designates the device in accordance with the first embodiment of the present invention. The device 10 comprises an elongated main hollow body 12 having a first cylindrical portion 14, a unitary connected middle conical portion 16, and a mouthpiece 18, which is unitary connected to the middle portion 16. A central opening 20 is formed in the body 12, extending from the mouthpiece opening 22, through the mouthpiece 18, conical portion 16, and the main body 14.

Figure 3:
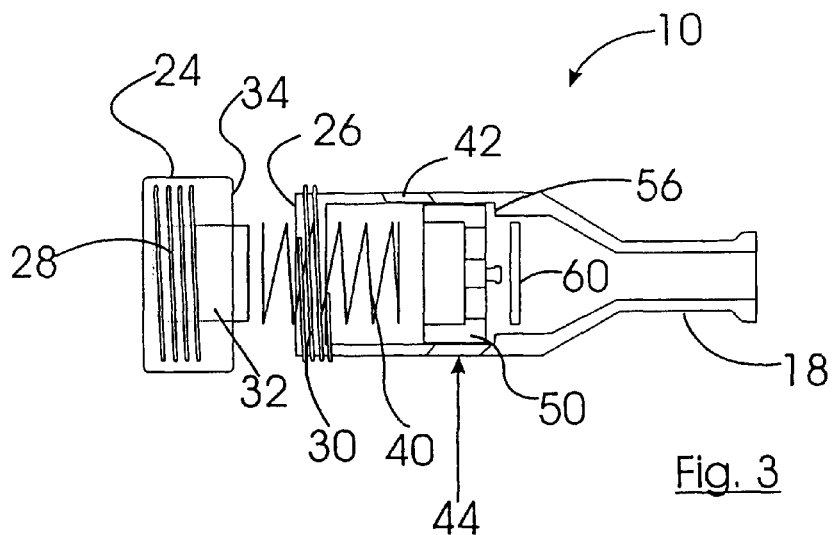
FIG. 3 is a longitudinal sectional view of the device of the first embodiment, with the adjustable cap being separated from the main body.

An adjustable screw cap 24 closes the normally closed end 26 of the main body portion 14. The cap 24 is provided with threads 28 on the inner wall of the cap. The threads 28 matingly engage with threads 30 on the exterior wall of the end 26. A central plug 32 is formed in the cap 24, the plug 32 extending outwardly from an inner end 34 of the cap 24. The end 34, as can be better seen in FIG. 3, forms an annular shoulder that provides a first abutting surface, against which a compression spring 40 abuts, as will be described in more detail below.

An intake port 42 is cut through the wall of the hollow body 12, and an exhalation port 44 is formed in the main body portion 14, at a location spaced apart from the intake port 42. Positioned between the ports 42 and 44 is an exhalation peep valve 50, which is shown in an open intake position in more detail in FIG. 7. The valve 50 is the same valve that is used in the first and second embodiments of the present invention; therefore, its description will be omitted when the second embodiment is described hereinafter.

The exhalation valve 50 is mounted on a support bracket, or frame 52 that is fitted inside the main body portion 14. The support bracket 52 is provided with an annular flange 54 that frictionally engages the inner wall of the main portion 14. The inner corner of the flange 54 provides a second abutting surface for the compression spring 40.

An inwardly extending shoulder 56 is formed on the inner wall of the main portion 14 adjacent to the area of connection between the main portion 14 and the conical portion 16. The shoulder forms a stop when the bracket 52, along with the peep valve 50 is forced against the shoulder 56.

Figure 2:
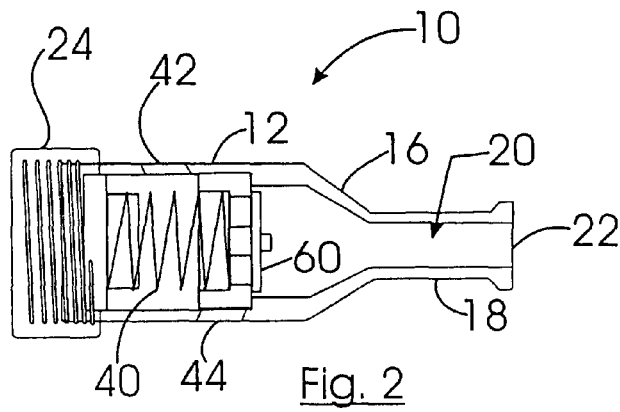
FIG. 2 is a longitudinal sectional view of the device shown in FIG. 1 showing the adjustable cap threadably engaged with the main body.

An intake valve 60 (FIG. 9) is mounted in the main portion 14 between an open end 22 and the bracket 52. The intake valve 60 can be as simple as a flexible rubber gasket that forms a one-way valve that opens during inhalation. The diameter of the circular intake valve 60 is smaller than the inner diameter of the opening 20 in the main portion 14, allowing some air to move around the intake valve 60. The intake valve, or flap 60 is made from a flexible material, for example latex. The flap lays over the ports of the piston/bracket 52 when pressure is against When the device 10 is assembled, the spring 40 abuts, at one of its ends, against the inner end, or shoulder 34, around the plug 32. The second end of the spring 40 abuts against the valve 50 mounted in the bracket 52, normally forcing the peep valve in a closed position shown in FIG. 2. The valve opens on intake of air, as shown in FIG. 8, but offers the pre-set resistance to a gas flow during exhalation.

When the user needs to exercise the muscles or simply distend airways, he closes his lips around the open end 22 of the mouthpiece 18. During inhalation, the air travels from the intake port 42, through the valve 50, around the valve 60, and into the open end 22 of the mouthpiece 18. On exhalation, the flow of gas is reversed, moving from the open end 22, around the valve 60, and against the resistance of the compression spring 40, into the directional exhalation port 44. In order for exhalation gas to exit the body 12, the user must exert sufficient pressure on the spring 40 to move the bracket 52 into a position away from the exit port 44 to allow the gas to be expelled.

Since the spring 40 offers resistance to the opening of the peep valve 50, a positive back pressure is created in the airways of the patient, forcing the patient to apply more force in exhaling, thereby strengthening the muscles involved in breathing. The cap 24, being in contact with the spring 40 can be screwed more or less tightly on the body 12, allowing adjustment for creation of positive pressure in the range of 5 cm to 20 cm of water. This range was found sufficient for most of the patients, although other pressure adjustments may be easily made if desired.

Turning now to the second embodiment shown in FIGS. 4–6, the nebulizer attachment device 70 is illustrated. The device 70 comprises an elongated, generally cylindrical body 72 that has a normally open end 74 and a normally closed end 76. An adjustable cam lever 78 is secured to a shaft connected to a piston 94 mounted in the end 76 to allow adjustment of the pressure required for opening and closing of the peep valve mounted inside the body 72. The pressure may be adjusted to a desired value, for example in the range of 5 cm to 10 cm of water, depending on the user's condition.

The adjustment may be accomplished by regulating position of the lever. For example, a first position would indicate pressure of 10 cm of water. By flipping the lever in an opposite direction, the user may regulate compression of the spring to create pressure of about 5 cm of water. Of course, the movement of the cam lever 78 may be calibrated to any pressure in between the desired range, setting different positions on the body 72 and indicating the setting by suitable indicia.

The body 72 is provided with a directional intake port 80 and a directional exhalation port 82. The open end 74 is adapted for frictional engagement with a manifold 84 that carries a mouthpiece 86 and a conventional nebulizer 88. The manifold 84, mouthpiece 86, and nebulizer 88 are not part of this invention; they are shown in phantom lines in FIG. 4.

Referring now to FIGS. 5 and 6, the interior of the device 70 is shown in more detail. As can be seen in FIG. 5, the body 72 is provided with a central opening 90 that extends from the open end 74 to the closing wall 92 of the closed end 76. The cam lever 78 is rotatably mounted on a shaft 77 (FIG. 6) that is fixedly attached to the wall 92 of the closed end 76. The piston 94 moves a small distance within the central opening 90 only to adjust compression of a spring 96.

The compression spring 96 is mounted between the piston member 94 and the exhalation valve peep valve 98. The valve 98 is similar is all respects to the valve 50 and, therefore its detail description is omitted here. The exhalation peep valve 98 allows creation of positive back pressure by forcing the patient to exhale against the force of the compressed spring 96. An intake valve, similar to the valve 60 is in the body 72 between the open end 74 and the valve 98.

During intake of air, the air travels through the port 80, through the valve 98 and intake valve 60 in the direction of arrow 100. During exhalation, or expiration, the air moves against the rubber gasket, or flap valve 60 that normally closes the ports of the piston/bracket. By continuing exhalation, the patient is able to move the bracket, against resistance of the compression spring 96, away from the exhalation port 82, allowing the gas to move through the exhalation peep valve 98 and through the exhalation port 82, in the direction of arrow 102, as shown in FIG. 6.

Once the adjustable cam lever 78 is set for the desired resistance to air movement, the device 70 is mounted on the manifold 84 and becomes connected to the nebulizer 88. A quantity of medication 104 deposited in the nebulizer 88 mixes with the air passing through the manifold 84 to the mouthpiece 86 and is delivered to the airways of the patient. The tiny droplets of medication dispersed by the aerosol-forming member 106 intercept the airflow passing through the body 72. The formed mist mixes with the intake airflow and is delivered into the airways of the user, extending the airways and reducing the asthma attack or other breathing problems of the patient.

It is preferred that during exhalation or inhalation, the patients keep their mouths firmly closed around mouthpieces 18 and 86, so as to seal the open ends of the devices 10 and 70 and to allow effective delivery of medication and exhalation of gases. When the patient exhales, the peep valve tends to distend airways of the patient and prevent collapsing of the alveoli by creating a positive back pressure.

When the air is forced to exit only through the exhalation valve that has been pre-set to offer resistance by a cap 24 or by the cam 78, the exhaust airflow cannot exit through the intake port and has to move through the exhalation ports 44 or 82. By keeping a sealed positive backpressure in the devices 10 and 70, the airways of the patients are kept open restoring the normal breathing. Once the pressure inside the inflamed sac is equalized with the pressure in a trachea, the medication has a much better chance to penetrating deep into the airways and cause dilation.

The devices 10 and 70 allow trapped carbon dioxide to escape through the exhalation ports 44 or 82, thereby reducing the toxic levels of carbon dioxide into the blood stream of the user. When the trapped gases are removed from the lungs, the lungs can then generate a greater inspiratory pressure with less effort of the patient.

Once the airways are extended, the pyramid effect establishes itself thus increasing the flow of much needed oxygenated air. The user, allowing pressure equalization and increase of volume in all lung areas, experiences a long expiratory phase. Once the airways are extended, the air movement into and out of the lungs is considerably improved. The lungs are not hyper-inflated; fresh air enters the lungs with more ease.

Additionally, if the attachment 70 is used, the medicine 104 is pulled in from the nebulizer 88 more effectively to reach the affected areas of the lungs and further dilate the airways. Consequently, the patient's collapsed or obstructed airways remain open and more precise medication delivery may be achieved. The treatment then becomes more effective with less medication.

The present invention can be used for patients suffering from asthma or emphysema. Many patients suffering from asthma have unexpected attacks and difficulty of getting to their medication. The attack may be enhanced by anxiety that the patient would suffocate before getting the medication. By having a small portable device readily available, the patient can at least restore some breathing and reduce the anxiety factor.

During an emphysema attack, the terminal bronchioles are weakened and are in a permanently enlarged condition. The alveolar walls are often times damaged. Because of the loss of alveolar space, the amount of surface area for gas exchange is reduced, and the elastic recoil of the lung tissue is diminished.

It is the lack of elasticity that causes inadequate lung recoil and fatigues inspiratory muscles. The lungs are unable to properly relax and return to their normal position. Under such conditions, patients are often advised to breathe with "pursed lips." By using, the sealed back pressure devices 10 or 70, that emphysema sufferers can increase delivery of air into the lungs and exhaust the carbon dioxide from the blood stream.

The backpressure created by the devices 10 and 70 prevents the bronchioles, alveoli from collapsing. The reduction of resultant hyperinflation allows the patient to inspire and exhale more fully, thereby delivering medication to a greater surface of the damaged tissue. Additionally, the sealed back pressure helps to keep the alveoli and airways open, allowing the release of the carbon dioxide from the lungs into the atmosphere. The effective removal of gas from the lungs and the blood stream improves the physiological function of the patient and allows more oxygen to be delivered into the lungs.

It is envisioned that the valve 10 and 70 can be preset to greater values than indicated above, particularly with patients having considerable problems with collapsed airways, although the preferred settings would range from about 5 cm to 20 cm of water.

It is envisioned that the devices of the present invention may be used for exercising the patients and restoring their ability to normally breathe. This is particularly true with a device 10 of the first embodiment. It is also envisioned that a nose clip and/or a molded cushioned mouthpiece may be used in combination with the mouthpieces to ensure a better seal of the patients' lips around the mouthpiece.

The device of the present invention can be inexpensively manufactured from readily available materials, such as plastic and lightweight metal. The springs 40 and 96 will naturally be manufactured from a material that is strong enough to withstand multiple compressions and expansions during use of the device. It is envisioned that the mouthpiece 18 may be manufactured to detachably engage the main body portion 14, if desired. In such a case, the device 10 with separated mouthpiece 18 may be carried in a compact space, such as the user's pocket, and engaged with the rest of the device, when needed.

The device 70 may be attached to a metered dose inhaler (MDI), instead of a nebulizer, if necessary. In such a case, a mini spacer would be used instead of the manifold 84. The mini spacer conventionally has a port for delivery of medication, for example anti-inflammatory drugs, in the form of a fine mist.

Many changes and modifications may be made in the design of the present invention without departing from the spirit thereof. I, therefore, pray that my rights to the present invention be limited only by the scope of the appended claims.

What is claimed is:

1. A sealed back pressure device for assisting a respiratory function of a patient, comprising:

an elongated hollow body having a first normally open end, a second normally closed end, an intake port formed through a wall of the hollow body and an exhalation port formed through the wall of the hollow body a distance from said intake port for communicating interior of the hollow body with the atmosphere;

a one-way exhalation valve mounted inside the hollow body for allowing exhaust gas to be exhaled through the exhalation port;

a compression spring mounted between the exhalation valve and the closed end for regulating resistance to gas flow being exhaled by the patient; and a means mounted on the second end of the hollow body for adjusting compression of the spring.

2. The device of claim 1, wherein said adjusting means comprises a cap detachably mounted on the second end, said cap providing a first abutting surface for said compression spring.

3. The device of claim 2, wherein said exhalation valve is supported by a frame mounted in the hollow body, said frame providing a second abutting surface for said compression spring.

4. The device of claim 2, wherein said cap is threadably engageable with the second end of the hollow body.

5. The device of claim 2, wherein said cap adjustably compresses said compression spring to maintain a positive back pressure of between 5 and 20 centimeters of water.

6. The device of claim 3, wherein said hollow body is provided with an annular shoulder extending into a central opening formed by the hollow body, and wherein said frame contacts said shoulder, thereby preventing sliding movement of the frame toward said open end.

7. The device of claim 1, wherein said open end is provided with a mouthpiece for engagement by lips of the patient.

8. The device of claim 1, wherein said hollow body is adapted for attachment to a nebulizer for establishing fluid communication between said hollow body and the nebulizer for delivery of medication to airways of the patient.

9. The device of claim 8, wherein said open end of the hollow body is detachably securable to the nebulizer.

* * * * *